US00PP15768P3

(12) United States Plant Patent
Herman et al.

(10) Patent No.: US PP15,768 P3
(45) Date of Patent: May 17, 2005

(54) *BETULA PAPYRIFERA* NAMED 'VAREN'

(50) Latin Name: *Betula papyrifera*
Varietal Denomination: Varen

(75) Inventors: Dale E. Herman, Fargo, ND (US); Larry J. Chaput, Fargo, ND (US); Zong-Ming Cheng, Knoxville, TN (US); Wenhao Dai, Fargo, ND (US)

(73) Assignee: NDSU Research Foundation, Fargo, ND (US)

( * ) Notice: Subject to any disclaimer, the term of this patent is extended or adjusted under 35 U.S.C. 154(b) by 58 days.

(21) Appl. No.: 10/377,136

(22) Filed: Feb. 26, 2003

(65) Prior Publication Data

US 2004/0168237 P1 Aug. 26, 2004

(51) Int. Cl.[7] ..... A01H 5/00
(52) U.S. Cl. ..... Plt./216
(58) Field of Search ..... Plt./216

*Primary Examiner*—Kent Bell
*Assistant Examiner*—Louanne Krawczewicz Myers
(74) *Attorney, Agent, or Firm*—Jondle & Associates P.C.

(57) ABSTRACT

'Varen' is a new cultivar of *Betula papyrifera* birch tree. This new cultivar has exceptional clear white bark and dark green leaves.

3 Drawing Sheets

Genus and species: *Betula papyrifera.*
Cultivar denomination: 'Varen'.

BACKGROUND OF THE INVENTION

The present invention comprises a new and distinct cultivar of birch tree, botanically known as *Betula papyrifera,* and hereinafter referred to by the cultivar name 'Varen'. 'Varen' is a product of a planned tree selection program which had the objective of creating a new cultivar of birch tree having high bronze birch borer resistance, good birch leafminer resistance and various aesthetic qualities which were originated in a controlled breeding program.

The new cultivar is a selection of *Betula papyrifera* which was discovered by Applicant among seedlings grown in the North Dakota State University Research Arboretum near Absaraka, N. Dak. The original seed was collected Aug. 10, 1976 from trees growing in the Killdeer Mountains approximately eight miles northwest of Killdeer, N. Dak. These *Betula papyrifera* trees were typical of the species. Seedlings were germinated in an NDSU greenhouse, potted in one-gallon containers for two years and then transplanted to the arboretum. As of 2004, the superior tree, 'Varen' is 27 years old. It was selected by virtue of its long-term, bronze birch borer resistance, exceptionally white bark, marked exfoliation of bark, quality dark green foliage, excellent golden-yellow autumn foliage coloration, and its upright, oblong-elliptical form, becoming more rounded with maturity. Because this selection is adapted to a dryer environment, both in annual precipitation (15–16 inches per year) and lower humidity levels, Applicant believes it will have greater stress tolerance than other named cultivars of *Betula papyrifera.*

The first act of asexual reproduction of 'Varen' was accomplished when plants were produced in tissue culture by Applicant from the initial selection on Mar. 10, 2000 in a controlled environment in Fargo, N. Dak. (NDSU). Horticultural examination of selected units initiated has demonstrated that the combination of characteristics as herein disclosed for 'Varen' are firmly fixed and reproduce true to type since 'Varen' will be propagated asexually or vegetatively, not by seed.

'Varen' has not been observed under all possible environment conditions. The phenotype may vary with variations in environment such as temperature, light intensity, and day length. The following observations, measurements and comparisons describe the plants grown in NDSU Research Arboretum or under greenhouse conditions, which approximate those generally used in commercial practices.

This new birch tree is illustrated by the accompanying photographs which show blooms, buds, and foliage of the plant in full color, the colors shown being as true as can be reasonably obtained by conventional photographic procedures.

DETAILED DESCRIPTION OF THE NEW PLANT

Figure 1:
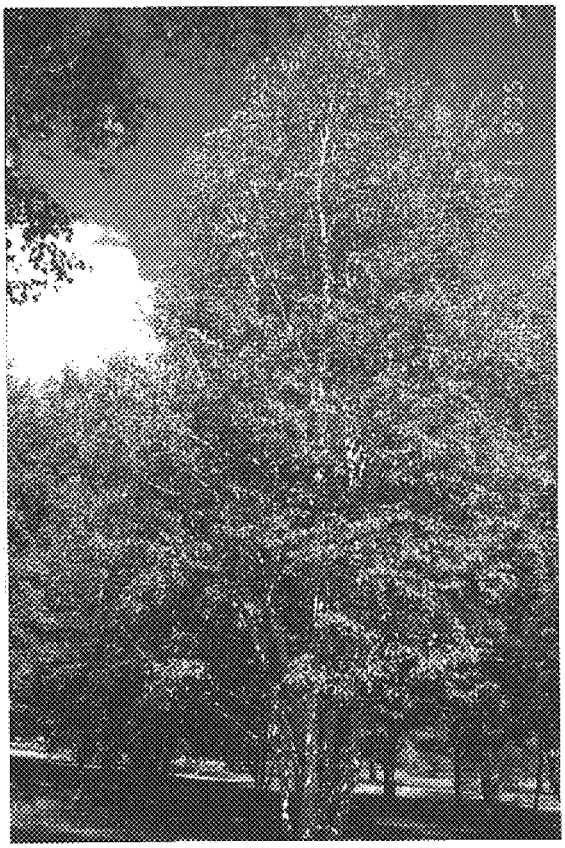
FIG. 1 shows overall tree with foliage.
Figure 2:
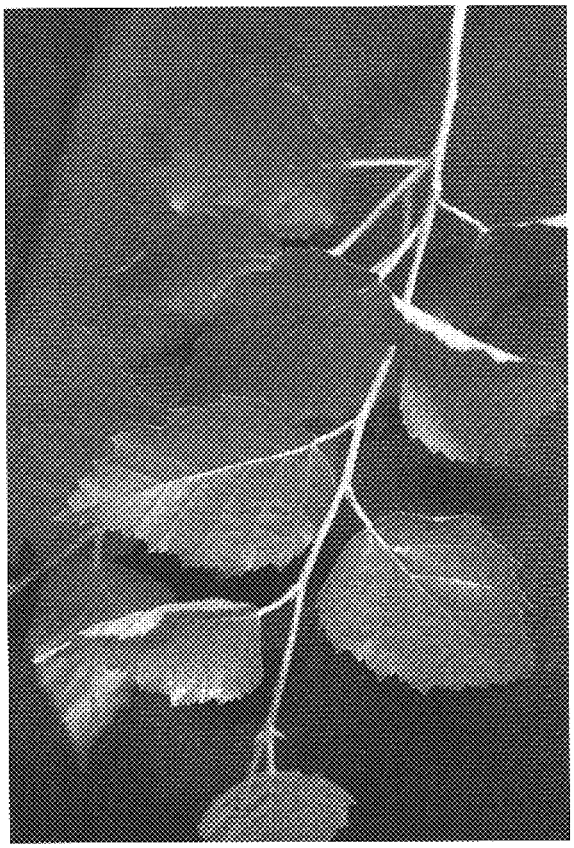
FIG. 2 shows a close-up of the leaves.
Figure 3:
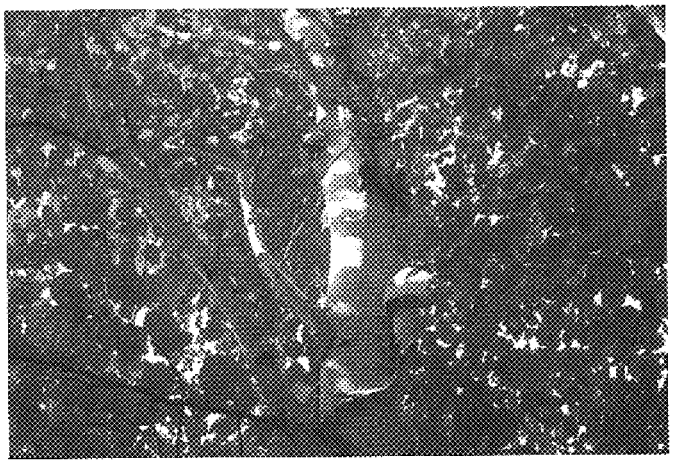
FIG. 3 shows the white, exfoliating bark.
Figure 4:
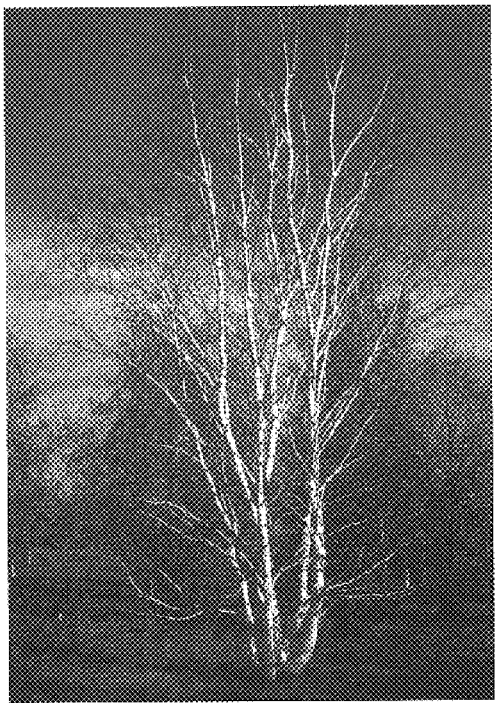
FIG. 4 shows the complete tree without foliage.
Figure 5:
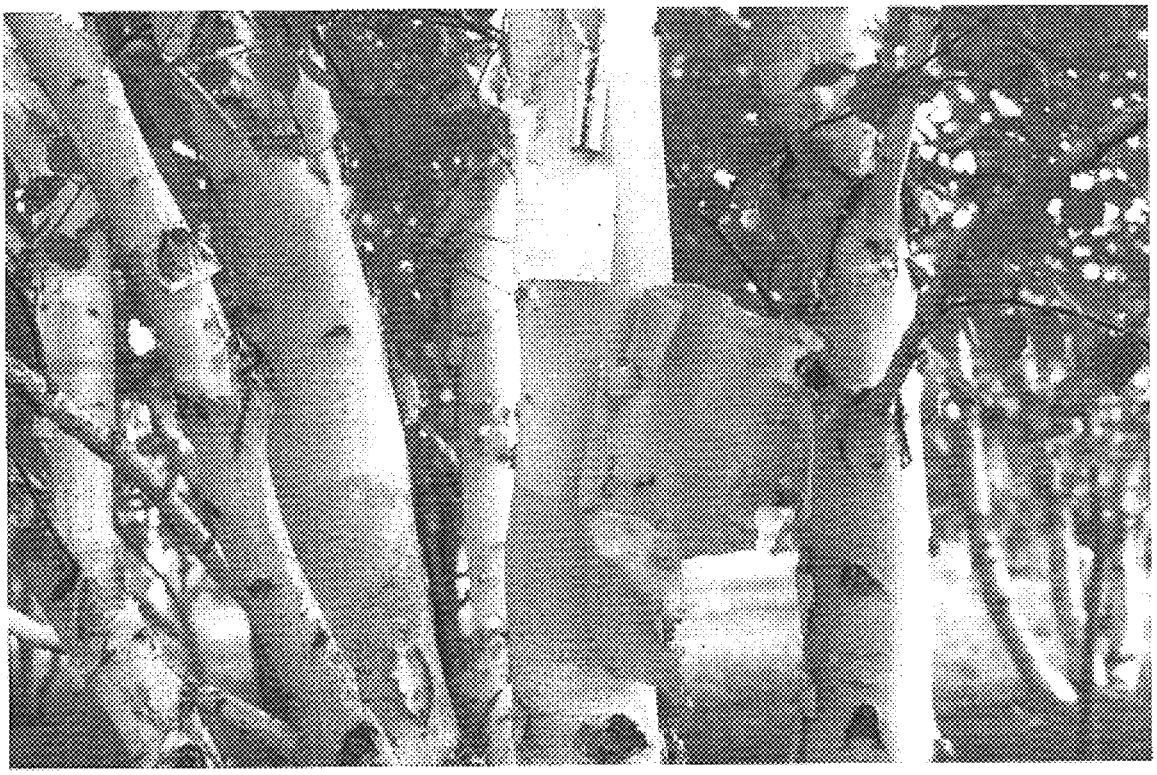
FIG. 5 is a close-up of the multiple trunks and exfoliating bark.

The following traits and characteristics describe the new cultivar.

Classification:

*Origin.*—Killdeer Mountains, eight miles northwest of Killdeer, N. Dak.
*Species.*—*Betula papyrifera.*
*Common names.*—Paper Birch.

TREE

Trunk:

*Multiple stem.*—Yes, five main trunks forming clump.
*Size.*—At 27 years of age, the sum total of five trunks is 75.9 cm or an average diameter of 15.2 cm per trunk.
*Bark.*—Exceptionally clear white bark. Plate 9-A1 to Plate 17-A1 (Maerz, A., et al., 1950, A Dictionary of Color, McGraw-Hill Book Co., Inc.) Bark exfoliates in sheets averaging 14.9 cm in length.

*Height.*—At 27 years of age, tree growing outdoors in NDSU Research Arboretum is 13.1 m high.

*Growth habit or form.*—Semi-pyramidal to upright, broadly oval.

*Growth rate.*—48.4 cm/year (under sod conditions in arboretum, no supplementary irrigation or fertilization).

Branches:

*Angle of attachment.*—Average angle of 26 branches, 49.5 degree.

*Spacing.*—Variable.

*Width.*—At 27 years of age, tree is 6.7 m wide.

*Lateral branches.*—At 27 years of age, four lateral branches measured at 160 cm off the ground had an average branch diameter of 3.2 cm. Distance between nodes on new annual growth average 3.2 cm.

*Bark.*—Prior to bark changing to white (See Trunk — Bark above) branches aged 3–7 years, range in color from greyed-orange (RHS 166A) to brown (RHS 200A to RHS 200B).

Lenticels:

*Size.*—On branches 2.54 cm in diameter, average length is 3.6 mm; average width is 0.3 mm. On branches 14.5 cm in diameter, average length is 10.1 mm; average width is 0.7 mm.

*Color.*—Black RHS 202A to 202C.

*Quantity.*—Many.

Foliage:

*Size of leaf.*—Length — Range 7–12 cm, average 9.2 cm. Width — Range 5.3–8.8 cm, average 6.5 cm.

*Shape of leaf.*—Ovate to broadly-ovate. Margin — Doubly-serrate.

*Leaf arrangement.*—Alternate. Branches with a diameter of 2.54 cm average 0.13 leaves per cm of lateral stem. The leaf apex is acuminate while the leaf base is gently rounded; however, scattered leaves are nearly flat or broadly wedge-shaped at the base.

*Pubescence distribution.*—Slightly pubescent on both leaf surfaces.

*Color.*—Upper side, RHS 137A (green). Underside, RHS 147B (yellow-green).

*Petiole.*—Length ranges from 2.0–3.6 cm, average length is 2.7 cm; average width is 1 mm; stipules absent. Ribs and veins — Average of 8 vein pairs per leaf. Thorns and spines — None. Buds — Imbricate, pointed, scattered hairs.

CATKINS

Staminate (male):

*Shape.*—Cylindrical, dormant stage fairly rigid, blooming stage, pendulous.

*Size.*—Dormant stage length ranges from 14–38 mm; average is 28 mm. Dormant stage width ranges from 6–8 mm; average is 6.6 mm. Blooming stage length ranges from 60–115 mm; average is 86 mm. Blooming stage width from 6–8 mm; average is 7 mm.

Scales (male):

*Shape.*—Teardrop to diamond-shaped, dormant stage.

*Size.*—2.0 mm.

*Color.*—RHS 200D (brown) to RHS 6C to RHS 6D (yellow).

Pistillate (female):

*Shape.*—Cylindrical; blooming stage, not pendulous.

*Size.*—Dormant stage length ranges from 13–18 mm; average is 16 mm. Dormant stage width ranges from 2–3 mm; average is 2.1 mm.

*Size.*—Blooming stage length ranges from 13–22 mm; average is 16 mm. Blooming stage width ranges from 7–10 mm; average is 8.5 mm.

Scales (female):

*Shape.*—Teardrop to diamond shaped.

*Size.*—1.1 mm.

*Color.*—RHS 149A (yellow-green) to RHS 144C (yellow-green).

Timing of appearance, staminate, and pistillate catkins:

*Staminate.*—Develop during summer.

*Pistillate.*—Develop May 5–20.

*Timing of anthesis.*—May 1–15, varies with year.

Fruit: Strobile bearing, many winged nutlets (seeds) which average 6 mm long and 3 mm wide.

*Shape.*—Cylindrical.

*Strobile length.*—4.3–5.1 cm, average 4.7 cm.

*Strobile width.*—0.9–1.2 cm, average 1.1 cm.

*Color.*—Mature color is brown, RHS 200D.

INSECT AND DISEASE RESISTANCE

No evidence of bronze birch borer attack in 27 years of evaluation in large birch collection in NDSU Research Arboretum where borer population is high. Resistance to birch leaf miner has been good to date.

COMPARISON WITH MOST SIMILAR CULTIVAR

Of the many commercial birch trees known to the Applicant, the most similar in comparison to 'Varen' are the other introduced *Betula papyrifera* cultivars such as;

*Betula papyrifera* 'Oenci' (U.S. Plant Pat. No. 12,766) with broad, pyramidal form, exfoliating white bark, young branches, red-mahogany color.

*Betula papyrifera* 'Cenci' (U.S. Plant Pat. No. 12,400) with tight oval, compact growth habit, peeling sheets of white bark.

*Betula papyrifera* 'Renci' (U.S. Plant Pat. No. 12,768) with narrowly pyramidal growth habit, non-exfoliating white bark.

*Betula papyrifera* 'Uenci' (U.S. Plant Pat. No. 12,767) with narrow upright growth habit, semi-exfoliating white bark exposing cinnamon under-layer.

'Chickadee' Paper Birch (unpatented) with narrow columnar-conical selection, white bark, introduced in Canada. Availability in nursery trade not know.

'Snowy' Paper Birch (unpatented) with multi-clonal seedling cultivar originating at Michigan State University. Availability in nursery trade and cultivar name not known. White bark, reputed bronze birch borer resistance.

What is claimed is:

1. A new and distinct *Betula papyrifera* birch tree as shown and described herein.

* * * * *